United States Patent [19]
Stewart et al.

[11] Patent Number: 5,935,932
[45] Date of Patent: Aug. 10, 1999

[54] BRADYKININ ANTAGONISTS CONTAINING PENTAFLUOROPHENYLALANINE

[75] Inventors: John M. Stewart; Lajos Gera, both of Denver, Colo.

[73] Assignee: University Technology Corporation, Boulder, Colo.

[21] Appl. No.: 09/096,716

[22] Filed: Jun. 12, 1998

Related U.S. Application Data

[60] Provisional application No. 60/049,571, Jun. 13, 1997.

[51] Int. Cl.$^6$ .......................... A61K 38/00; A61K 38/08
[52] U.S. Cl. .......................... 514/15; 530/314; 530/328; 930/21; 930/23
[58] Field of Search .............................. 514/15; 530/314, 530/328

[56] References Cited

U.S. PATENT DOCUMENTS 4,693,993  9/1987  Stewart ...................................... 514/14

OTHER PUBLICATIONS

Bhoola, et al., 44 *Pharmacol Revs.* 1 (1992).
Stewart, 42S *Agents Actions* 145 (1993).
Marceau, 30 *Immunopharmacol.* 1 (1995).
Sakata, et al., 33 *Immunopharmacol* 377 (1996).
Vavrek and Stewart, 6 *Peptides* 161 (1985).
Stewart and Vavrek, Bradykinin Antagonists, Burch RM, Ed., Pergamon, Oxford 51 (1991).
Regoli, et al., 123 *Eur. J. Pharmacol* 61 (1986).
Regoli, et al., 55 *Can J. Physiol Pharmacol* 855 (1977).
Perkins, et al., 53 *Pain* 191 (1993).
Hock, et al., 102 *Brit J Pharmacol* 769 (1991).
Cheronis, et al., 35 *J Med Chem* 1563 (1992).
Kyle, et al., 36 *J Med Chem* 1450 (1993).
Stewart, et al., 33 *Immunopharmacol* 51 (1996).
Whalley, et al., 75 *Can J Physiol Pharmacol* 629 (1997).
Tallett, et al., 17 *Peptides* 665 (1996).
Woll and Rozengurt, 85 *Proc Nat Acad Sci US* 1859 (1988).
Staley, et al., 12 *Peptides* 145 (1991).
Bunn, et al., 54 *Cancer Res* 3602 (1994).
Chan, et al., 33 *Immunopharmacology* 201 (1996).
Stewart and Young, *Solid Phase Peptide Synthesis*, Pierce Chemical Company (1984).
Stewart, 27 *Brazil J. Med. Biol. Res.* 1699 (1994).
Stewart and Gera, Maia LS, *Peptides* 1994 617, ESCOM, Leiden (1994).
Stewart and Gera, 33 *Immunopharmacology* 174 (1996).
Hill and Dunn, 30 *J. Org. Chem.* 1321 (1969).
Itoh, et al., *Tet. Lett.* 4393 (1975).
Porter and Shive, 11 *J. Am. Chem. Soc.* 402 (1968).
Hoffman, et al., 100 *J. Am. Chem. Soc.* 3585 (1978).
Skiles, et al., 35 *J. Med. Chem.* 4795 (1992).
Sasaki and Coy, 8 *Peptides* 119 (1987).
Trautshold, *Handbook of Expt. Pharmacol.* vol. 25, Springer Verlag pp. 53–55 (1970).
Roblero, et al., 6 *Res. Comm. Chem. Pathol* 207 (1973).

*Primary Examiner*—Cecilia J. Tsang
*Assistant Examiner*—Michael Borin
*Attorney, Agent, or Firm*—Kristine H. Johnson; Macheledt Bales & Johnson LLP

[57] ABSTRACT

The present invention provides bradykin antagonists containing pentafluorophenylalanine which are therapeutically useful. Moreover, the present invention provides methods to antagonize bradykinin receptors in a mammal in need of such antagonism, comprising administering a bradykinin antagonist containing pentafluorophenylalanine. Also provided are methods to treat inflammation in a mammal in need of such inhibition, comprising administering a bradykinin antagonist containing pentafluorophenylalanine. Lastly, a method to treat cancer in a mammal in need of such inhibition, comprising administering a bradykinin antagonist containing pentafluorophenylalanine.

31 Claims, No Drawings

BRADYKININ ANTAGONISTS CONTAINING PENTAFLUOROPHENYLALANINE

This application claims benefit of U.S. Provisional Patent Application Ser. No. 60/049,571, filed on Jun. 13, 1997.

BACKGROUND OF THE INVENTION

The nonapeptide bradykinin (BK) and the homologous decapeptide kallidin (Lys-BK) are produced endogenously by enzymatic cleavage by plasma and tissue kallikreins of their circulating precursor proteins (kininogens) in many tissues and under a wide variety of conditions for regulation of both normal and abnormal physiology. Bhoola et al., 44 *Pharmacol Revs.* 1 (1992). In addition to their functions in regulation of normal physiology, there is considerable evidence to support the hypothesis that these peptides (collectively called kinins) are the initiators of most, if not all, inflammation. Stewart, 42S *Agents Actions* 145 (1993). Trauma, infection and allergic reactions have all been shown to stimulate kinin release; the kinins then stimulate release of the further chain of inflammatory mediators, such as prostaglandins, TNF and various interleukins. A decade of animal studies and recent clinical trials have indicated that BK antagonists may become important drugs for anti-inflammatory medicine.

Under normal conditions, actions of kinins are transitory in vivo, due to rapid cleavage of the peptides by several enzymes. The most important of these are angiotensin converting enzyme (ACE; Kininase II), localized principally to the endothelium of the pulmonary vasculature, and the soluble circulating carboxypeptidase N (CPN; kininase I). The membrane-bound enkephalinase (endopeptidase 3.4.24.11) and aminopeptidase P (APP) are less active toward the kinins. ACE removes the C-terminal dipeptide from BK, yielding BK-(1–7), which is inactive biologically. The products of CPN action, BK-(1–8) and kallidin-(1–9), while inactive at B2 receptors, are the normal ligands for B1 receptors. Products of cleavage by APP and endopeptidase 24.11 are totally inactive. ACE normally cleaves more than 99% of BK on a single passage through the pulmonary circulation, and CPN normally causes BK to have a plasma half-life of 15 seconds or less.

Biological actions of kinins are mediated by two classes of receptors: B1 and B2. Both classes of receptors have been cloned and sequenced from a variety of species. They are typical G protein-coupled receptors having seven putative helical membrane-spanning segments. In various tissues, BK receptors are coupled to every known second messenger system. Prominent among these, and particularly important in inflammation, are phospholipase A2 (PLA2), with subsequent production of prostaglandins and leukotrienes, and phospholipase C (PLC), with subsequent stimulation of cell proliferation, for wound healing. B2 receptors are constitutively expressed on the membranes of most cells, and require the full chain of the kinin peptides, including the C-terminal arginine residue, for binding and activation. In contrast, B1 receptors are not normally expressed in most tissues; their expression is stimulated in inflammation. Marceau, 30 *Immunopharmacol.* 1 (1995). Activation by kinins of vascular B1 and B2 receptors causes vasodilation and lowering of blood pressure. The severe fall in blood pressure (shock) of systemic bacterial infection appears to be initiated and sustained by production of BK. Bacterial enzymes produce BK, either by direct cleavage of circulating kininogens or by activation of kallikreins which then cleave kininogens. Sakada, et al., 33 *Immunopharmacol* 377 (1996). The lipopolysaccharide (LPS) endotoxin of Gram-negative bacterial cell walls also stimulates production of BK and initiates release of TNF and lymphokines. A particularly vicious aspect of infection is that ACE is lost from the pulmonary circulation, causing kinins to be metabolized principally by CPN, thus producing large amounts of the ligands for the concomitantly induced B1 receptors and causing shock.

Antagonists for BK B2 receptors were introduced in 1984 (Vavrek and Stewart, 6 *Peptides* 161 (1985) and stimulated a renaissance of kinin research. Rapid metabolism of kinins had made demonstration of physiological and pathophysiological roles for kinins very difficult. With tools available to block kinin receptors, demonstrations of participation of kinins in regulation of every major physiological system and initiation or mediation of much pathophysiology soon followed. The essential structural change in the BK molecule for production of antagonists was replacement of the 7-proline residue by a D-aromatic amino acid, most commonly D-Phe. This change yielded a weak partial antagonist. Additional changes to increase receptor affinity and decrease enzyme degradation yielded the useful "first generation" B2 antagonists (NPC-349; see Table 1). These antagonists had low affinity for BK receptors and showed short activity in vivo, due to cleavage by CPN. Stewart and Vavrek in "Bradykinin Antagonists,: Burch RM, Ed., Pergamon, Oxford 51 (1990). Regoli et al., 123 *Eur. J. Pharmacol* 61 (1986).

Although B1 antagonists had been described earlier (Regoli et al., 55 *Can J. Physiol Pharmacol* 855 (1977), they did not attract much interest until the demonstration that B1 receptors, normally not present in most tissues, are expressed in chronic inflammation. Perkins et al., 53 *Pain* 191 (1993); Marceau, 30 *Immunopharmacol.* 1 (1995). Replacement of the C-terminal phenylalanine in the normal B1 ligands [BK-(1–8) and kallidin-(1–9)] by a hydrophobic aliphatic amino acid yielded the first B1 antagonists. An example is [Leu8]-BK(1–8). The "first generation" B1 antagonists, like the earliest B2 antagonists, were rapidly degraded in vivo.

The "second generation" of B2 antagonists was begun with introduction by Hoechst investigators of Icatibant (HOE-140) (Hock et al., 102 *Brit J Pharmacol* 769 (1991) and followed by the Cortech Bradycor (CP-0127) (Cheronis et al., 35 *J Med Chem* 1563 (1992) (see Table 1). In the first generation B2 antagonists, such as the Stewart NPC-349, although the D-amino acid residue at position seven blocked action of ACE, and the N-terminal D-arginine residue blocked aminopeptidase action, these antagonists were still degraded by plasma CPN and by endopeptidase 24.11. Indeed, the first generation B2 antagonists, such as NPC-349, showed B1 antagonist activity in vivo, due to enzymatic removal of the C-terminal arginine (Regoli et al., 123 *Eur. J. Pharmacol* 61 (1986). The significant structural feature of Icatibant is the incorporation of imino acids, which greatly restrict peptide conformation and inhibit enzyme action, at positions seven and eight. Incorporation of octahydroindolecarboxylic acid (Oic) at position eight made this peptide resistant to cleavage by CPN and thus greatly extended its in vivo activity. The bulky D-tetrahydroisoquinolinecarboxylic acid (Tic) at position seven, combined with Oic8, strongly restricts the conformational freedom of the important carboxyl end of the peptide to a shape evidently preferred by the B2 receptors. Kyle et al., 36 *J Med Chem* 1450 (1993). The very hydrophobic nature of these residues is probably also important, causing Icatibant to have a slow "on-time" and a very long persistence at or near receptors. Bradycor owes its increased potency to its dimeric nature, with perhaps some additional contribution from the hydrophobic character of the linker moiety. Despite these improvements, both of these antagonists are slowly degraded by plasma and tissue extracts. Endopeptidase 24.11 is probably important in this degradation.

Recently a dramatic improvement (the "third generation" of BK antagonists) came with introduction of α-(2-indanyl) glycine (Igl) into the antagonist structure. Stewart et al., 33 *Immunopharmacol* 51 (1996). An extremely interesting peptide is B9430, which has L-Igl at position five, D-Igl at position seven, and Oic at position eight. This antagonist shows truly impressive high potency and long duration of action in vivo. The Igl residue at position five evidently blocks degradation by endopeptidase 24.11. These new antagonists persist more than six hours in plasma and tissue homogenates, and show very long duration of action in vivo. A single intravenous injection of B9430 in rats blocks the hypotensive action of BK for more than four hours, a subcutaneous injection in rats can block BK action for 48 hours, and a subcutaneous injection in rabbits blocks BK action for more than 24 hrs. Perhaps the most remarkable property of the antagonists containing Igl is their high potency at B1 receptors, in addition to the anticipated B2 activity, although they contain the C-terminal arginine residue that normally prevents B1 receptor activity of agonists and antagonists. Activity of these new antagonists at both receptors has been demonstrated in cultured cells, in isolated smooth muscle tissues, and in vivo. They are active at human B1 and B2 receptors. Most recently, B9430 has been shown to be active following intragastric administration in rats, although the bioavailability is low. Whalley et al., 75 *Can J Physiol Pharmacol* 629 (1997). This result suggests that we may have made progress on the way toward the ambitious goal of a chemically modified peptide having significant oral activity.

Bradykinin has important growth factor activity, although the lability of BK has made demonstration of this property difficult. Production of BK in trauma (BK is produced whenever blood clotting is initiated) is probably to stimulate wound repair, where it can act in concert with platelet-derived growth factor. Recent papers have begun to delineate the intracellular events, especially tyrosine phosphorylation, that follow action of BK on cells. Tallett et al., 17 *Peptides* 665 (1996). Small cell lung cancer (SCLC) cells express BK receptors, and evidently use BK and other peptides (substance P, bombesin) as growth stimulants. Woll and Rozengurt, 85 *Proc Nat Acad Sci US* 1859 (1988). Several peptide antagonists have been tested as potential inhibitors of SCLC growth, and some progress has been reported. Staley et al., 12 *Peptides* 145 (1991). Our BK antagonists have been tested consistently by Dan Chan at the University of Colorado Cancer Center for their effects on cultured cells of SCLC. While all our good antagonists, especially the new "third generation" peptides, block the BK-evoked increase in intracellular calcium concentration (Bunn et al., 54 *Cancer Res* 3602 (1994), they do not inhibit cell growth. Most recently, however, dimers of our new antagonists, such as B9870, were found to inhibit growth of cultured SCLC cells. Chan et al., 33 *Immunopharmacol* 201 (1996).

SUMMARY OF THE INVENTION

It is therefore an object of the present invention to provide bradykinin antagonists containing pentafluorophenylalanine which are therapeutically useful.

Specifically, it is an object of the present invention to provide the following pentafluorophenylalanine-containing bradykinin antagonists:

$R_2$-$R_1$-A-B-C-D-E-F-G-H-I-J     [Formula I]

wherein:
$R_2$ is absent, or $GUN_2$; $R_1$ is absent, Lys, Aca or bApg; A is DArg, Lys or Arg; B is Arg;
C is Pro or NMF; D is Hyp, Pro, Igl or DIgl; E is Gly; F is Igl, Thi, f5f or Cpg; G is Ser;
H is Df5f, DIgl or DTic; I is Oic, Igl, Thi, NchG, f5f, Leu, Chg or Nc7G; and J is Arg, provided that, at least one of F, H or I must be f5f or Df5f.

Dimers of the above compounds are also provided and of the following composition:

[Formula I]-X-[Formula I]     {Formula II} except when $R_2$ is $Gun_2$ or when $R_1$ is Aca or bApg, and wherein X is α-DDD or EGS.

It is further an object to provide methods to antagonize bradykinin receptors in a mammal in need of such antagonism, comprising administering a bradykinin antagonist containing pentafluorophenylalanine.

It is a further object to provide methods to treat inflammation in a mammal in need of such inhibition, comprising administering a bradykinin antagonist containing pentafluorophenylalanine.

It is further an object to treat cancer in a mammal in need of such inhibition, comprising administering a bradykinin antagonist containing pentafluorophenylalanine.

Other objects and features of the present invention will be apparent from the following detailed description of the invention.

Definitions

The following abbreviations have the following meanings in this specification:
1. Aca=1-Adamantanecarboxyl-
2. bApG=N,N-bis(3-aminopropyl)-glycine
3. Chg=α-Cyclohexylglycine
4. Cpg=α-Cyclopentylglycine
5. DDD=Dodecanedioyl-
6. EGS=Ethylene glycol bis-succinyl-
7. f5f=Pentafluorophenylalanine
8. Gun=Guanidyl-
9. Hyp=4-Hydroxyproline
10. Igl=α-(2-Indanyl)-glycine
11. NchG=N-Cyclohexylglycine
12. Nc7G=N-Cycloheptylglycine
13. NMF=N-Methylphenylalanine
14. Oic=Octahydroindole-2-carboxylic acid
15. Thi=β-(2-Thienyl)-alanine
16. Tic=Tetrahydroisoquinoline-3-carboxylic acid
17. Cpg—R—Arg=Pseudo Cpg-Arg; C═O>CH2

All other amino acid or other abbreviations shall have the meanings generally recognized in the art.

DETAILED DESCRIPTION OF THE INVENTION

The present invention discloses compounds of the formula:

$R_2$-$R_1$-A-B-C-D-E-F-G-H-I-J     [Formula I]

wherein:
$R_2$ is absent, or $GUN_2$; $R_1$ is absent, Lys, Aca or bApg; A is DArg, Lys or Arg; B is Arg;

C is Pro or NMF; D is Hyp, Pro, Igl or DIgl; E is Gly; F is Igl, Thi, f5f or Cpg; G is Ser;

H is Df5f, DIgl or DTic; I is Oic, Igl, Thi, NchG, f5f, Leu, Chg or Nc7G; and J is Arg, provided that, at least one of F, H or I must be f5f or Df5f.

Dimers of the above compounds are also provided and are of the following composition:

[Formula I]-X-[Formula I]  {Formula II} except when $R_2$ is $Gun_2$ or when $R_1$ is Aca or bApg, and wherein X is α-DDD or EGS.

In particular the following compounds are within the scope of the present invention:

B10044 DArg-Arg-Pro-Hyp-Gly-Igl-Ser-Df5f-Oic-Arg

B10056 DArg-Arg-Pro-Hyp-Gly-Igl-Ser-Df5f-Igl-Arg

B10058 DArg-Arg-Pro-Hyp-Gly-Igl-Ser-Df5f-Thi-Arg

B10112 DArg-Arg-Pro-Hyp-Gly-Igl-Ser-Df5f-NchG-Arg

B10116 DArg-Arg-Pro-Hyp-Gly-Igl-Ser-Df5f-Oic-Arg

B10118 αDDD-(Lys-DArg-Arg-Pro-Pro-Gly-Thi-Ser-Df5f-Oic-Arg)2

B10146 Lys-Lys-Arg-Pro-Hyp-Gly-Igl-Ser-Df5f-Chg

B10148 Lys-Lys-Arg-Pro-Hyp-Gly-Igl-Ser-Df5f-Oic

B10150 DArg-Arg-NMF-Hyp-Gly-Igl-Ser-Df5f-Oic-Arg

B10154 Aca-DArg-Arg-Pro-Hyp-Gly-Igl-Ser-Df5f-Oic-Arg

B10156 Gun2-bApg-DArg-Arg-Pro-Hyp-Gly-Igl-Ser-Df5f-Oic-Arg

B10158 αDDD-(Lys-Darg-Arg-Pro-Hyp-Gly-Igl-Ser-Df5f-Oic-Arg)2

B10164 DArg-Arg-Pro-Hyp-Gly-f5f-Ser-DIgl-Oic-Arg

B10166 DArg-Arg-Pro-Hyp-Gly-Thi-Ser-Df5f-f5f-Arg

B10168 DArg-Arg-Pro-Hyp-Gly-Thi-Ser-DTic-f5f-Arg

B10172 DArg-Arg-Pro-Hyp-Gly-Thi-Ser-Df5f-Leu-Arg

B10174 DArg-Arg-Pro-Hyp-Gly-Igl-Ser-Df5f-Leu-Arg

B10178 DArg-Arg-Pro-Hyp-Gly-Igl-Ser-DIgl-f5f-Arg

B10180 DArg-Arg-Pro-Hyp-Gly-Igl-Ser-Df5f-Chg-Arg

B10186 DArg-Arg-Pro-Hyp-Gly-Cpg-Ser-Df5f-Cpg-R-Arg

B10196 DArg-Arg-Pro-Hyp-Gly-Igl-Ser-Df5f-Cpg-Arg

B10204 DArg-Arg-Pro-Hyp-Gly-Thi-Ser-Df5f-Nc7G-Arg

B10206 DArg-Arg-Pro-Hyp-Gly-Igl-Ser-Df5f-Nc7G-Arg

B10208 DArg-Arg-Pro-Hyp-Gly-Thi-Ser-Df5f-NchG-Arg

B10210 DArg-Arg-Pro-Hyp-Gly-f5f-Ser-DIgl-Oic-Arg

B10214 DArg-Arg-Pro-Igl-Gly-Igl-Ser-Df5f-Oic-Arg

B10216 DArg-Arg-Pro-DIgl-Gly-Igl-Ser-Df5f-Oic-Arg

B10230 Arg-Arg-Pro-Hyp-Gly-Igl-Ser-Df5f-f5f-Arg

B10232 DArg-Arg-Pro-Hyp-Gly-Igl-Ser-Df5f-f5f-Arg

B10234 DDD-(DArg-Arg-Pro-Hyp-Gly-Igl-Ser-Df5f-f5f-Arg)2

B10236 EGS-(Arg-Arg-Pro-Hyp-Gly-Igl-Ser-Df5f-f5f-Arg)2

B10254 EGS-(DArg-Arg-Pro-Hyp-Gly-Igl-Ser-Df5f-Nc7G-Arg)2

B10274 DArg-Arg-Pro-Hyp-Gly-f5f-Ser-Df5f-f5f-Arg

The present peptides may be synthesized by any method known in the art, but preferably by the solid phase method, generally using Boc-amino acids and conventional side-chain blocking groups (Stewart & Young, *Solid Phase Peptide Synthesis*, Pierce Chemical Company (1984). Incorporation of the sterically hindered amino acids requires use of efficient coupling agents, such as BOP-HOBt, TBTU or HBTU. Peptides can then be purified by countercurrent distribution followed by preparative HPLC as needed. For exploratory incorporation of novel optically active amino acids, the racemic amino acid is incorporated into the peptide and the two diasteromeric peptides are separated by HPLC. For synthesis of larger amounts, the new amino acids can be resolved enzymatically to optical homogeneity. Peptides can be characterized by amino acid analysis, TLC, and laser desorption mass spectroscopy (LDMS). The 'found molecular weight' can be used for accurate calculation of molar doses for biological experiments.

Boc-D-f5f and Boc-L-f5f can be purchased from Advanced Chemtech (Louisville, Ky.) and are available to those in the art.

Moreover, methods to antagonize bradykinin receptors in a mammal in need of such antagonism, comprising administering a compound of the Formulas I or II are within the scope of the present invention. The preferred method is one wherein the mammal in which the bradykinin receptors are antagonized is a human.

Furthermore, as those in the art are aware, compounds with bradykinin antagonist activity are useful to treat a number of disease states. Bradykin has been associated with the following pathological conditions: septic shock; asthma; serious trauma (ie. head, spinal cord injuries); inflammatory joint disease (ie. rheumatoid arthritis, carpal tunnel syndrome); inflammatory bowel disease (ie. IBD, ulcerative colitis, Crohn's disease); asthma; allergic rhinitis; pelvic inflammatory disease, stroke and reperfusion injury and other conditions associated with the inflammatory process. A review of these disease states associated with bradykinin can be found at Stewart, 27 *Brazil J. Med. Biol. Res.* 1699 (1994).

Moreover, it has recently been shown that certain bradykinin antagonists are effective at killing small cell lung cancer cells. Chan et al., 33 *Immunopharmacology* 201 (1996). For this reason, the present invention also encompasses methods to treat disease states associated with excess bradykinin production. Specifically, a method to treat inflammation in a mammal in need of such treatment comprising administering a pharmaceutically-effective amount of a compound of Formulas I or II is disclosed. Also disclosed is a method to treat cancer in a mammal in need of such treatment comprising administering a pharmaceutically-effective amount of a compound of Formulas I or II.

These compounds may be administered in any formulation which allows the bradykinin-associated condition to be treated. Moreover, the compounds and/or formulations may be administered via any acceptable method or route. For example, the compounds and/or formulations may be administered via liquid or solid (ie. powder), intravenously, transdermally, sublingually, via tablet, pill, powder, lozenge, sachet, cachet, elixir, suspension, emulsion, solution, syrup, aerosol (as a solid or in a liquid medium), ointment, soft or hard gelatin capsule, suppository, sterile injectable solution, sterile packaged powder and transdermal patch, so long as the bradykinin response is thereby affected.

(ethylene glycolbis-[succinimidylsuccinate]) (EGS; from Pierce) linker were allowed to react overnight in DMF. The resulting peptide dimers were then purified by preparative reversed-phase HPLC.

5. Unusual amino acids:

a. D- and L-α-Cyclopentylglycine were prepared in our laboratory by the literature method of Hill and Dunn, 30 *J. Org. Chem.* 1321 (1969). Both D- and L- isomers were converted to the N-Boc derivative by the standard procedure with BOC-ON/DEA in dioxane according to Itoh et al., *Tet. Lett.* 4393 (1975).

Boc-D-Cpg: mp.: 90–92° C. (Ether/hexane); $[\alpha]_D^{26}$=+2.84 (c 2.5 EtOH)

TABLE 1

Structures of Bradykinin and Representative Antagonists

| | |
|---|---|
| Bradykinin (BK) | Arg-Pro-Pro-Gly-Phe-Ser-Pro-Phe-Arg |
| BK (1-8) (B1 agonist) | Arg-Pro-Pro-Gly-Phe-Ser-Pro-Phe |
| B1 Antagonist | Arg-Pro-Pro-Gly-Phe-Ser-Pro-Leu |
| NPC-349 | DArg-Arg-Pro-Hyp-Gly-Thi-Ser-DPhe-Thi-Arg |
| HOE-140 | Darg-Arg-Pro-Hyp-Gly-Thi-Ser-DTic-Oic-Arg |
| B9430 (B2 and B1 antag.) | DArg-Arg-Pro-Hyp-Gly-Igl-Ser-DIgl-Oic-Arg |
| B9858 (B1 antagonist) | Lys-Lys-Arg-Pro-Hyp-Gly-Igl-Ser-DIgl-Oic |
| B10056 | DArg-Arg-Pro-Hyp-Gly-Igl-Ser-Df5f-Igl-Arg |
| B10274 | DArg-Arg-Pro-Hyp-Gly-f5f-Ser-Df5f-f5f-Arg |

Is to be noted that certain changes and modifications are apparent to those skilled in the art. Such changes and modifications are to be understood as included within the scope of the present invention.

EXAMPLES

1. Synthesis—General

Peptides were synthesized by standard solid phase methods, according to Stewart & Young, *Solid Phase Peptide Synthesis*, Rockford Ill.: Pierce Chemical Company (1984), purified by countercurrent distribution and/or HPLC and characterized by HPLC, TLC, paper electrophoresis, mass spectroscopy and amino acid analysis. DCC was used for coupling of normal amino acids, and BOP-HOBt, TBTU or HATU were used for sterically hindered residues.

2. Synthesis of B10154: This is an example of N-terminal acylation. In this case, peptide resin was acylated with pre-activated acid in DMF according to the procedure of Stewart and Gera in Maia LS Ed., *Peptides* 1994 617, ESCOM, Leiden (1994).

3. Synthesis of B10156: This is an example of N-terminal guanylation. In this case, peptide resin was guanylated with a 4-fold excess of N,N'-bis-Cbz-1-guanylpyrazole according to Stewart and Gera, 33 *Immunopharmacology* 174 (1996).

4. Dimerization:

Method A (B10118, B10158 and B10234): To 0.05 mmole neutralized peptide resin, N,N-diisopropyl-ethylamine (0.15 mmole, 26.13 μL) and dodecanedioyl dichloride (0.026 mmole, 6.65 μL) was added in dichloromethane (2.5 mL) and stirred for 6–12 hours. The resin was washed with DCM and ethanol. The dried peptide was cleaved from the resin with HF. The free peptides were extracted with acetic acid, lyophilized and purified by HPLC.

Method B (10236 and B10254): One equivalent of peptide monomer salt, 10 equivalents DIEA and 0.55 equivalent Boc-L-Cpg: mp.: 90–92° C. (Ether/hexane); $[\alpha]_D^{25}$=−3.04 (c 2.5 EtOH)

These compounds may also be obtained from Peninsula: #16161 and 15161.

b. D, L -α-(2-Indanyl)glycine) (Igl) was made from 2-bromoindane and ethyl acetamidocyanoacetate as described in the literature in Porter and Shive, 11 *J. Am. Chem. Soc.* 402 (1968). It was then resolved by enzymatic hydrolysis of the N-acetyl derivative with hog kidney acylase 1. The N-Boc protection of Igl was accomplished by a general method (Hoffman et al, 100 *J. Am. Chem. Soc.* 3585 (1978)) in DMF/H$_2$O at pH 8–9 using 1N NaOH.

Boc-L-2-Igl: mp.: 86–89° C. (dec.) (ether-hexane); $[\alpha]_D^{25}$=+16.9 (c 2.0, EtOH)

Boc-D-2-Igl: mp.: 86–89° C. (dec.) (ether-hexane); $[\alpha]_D^{22}$=−17.2 (c 2.0, EtOH)

These compounds may also be purchased from Peninsula (#16160 and #15160) or from Synthetech, Inc.

c. N-Cyclohexylglycine (NchG) and N-cycloheptylglycine (Nc7G) were made by reductive amination or cyclohexanone or cycloheptanone with glycine methyl ester according to the N-(2-indanyl)-glycine procedure of Stewart and Gera, 33 *Immunopharmacology* 174 (1996) and Skiles et al, 35 *J. Med. Chem.* 4795 (1992).

Boc-NchG: mp: 101–103° C.

Boc-Nc7G: mp: 89–90° C.

d. Boc-D-pentaflurophenylalanine (Boc-Df5f) and Boc-L-pentaflurophenylalanine (Boc-f5f) were purchased from Advanced Chemtech (#BF3446 and #2446).

e. α-Cyclohexylglycine (Chg) was purchased from Chem-Impex (#02561) and was converted to Boc-Chg (mp: 82–85° C.).

f. The reduced peptide bond for analog B10196 was introduced by reductive alkylation of Arg(Tos)-resin by Boccyclopentylglycine aldehyde by the procedure in Stewart and Gera, 33 *Immunopharmacology* 174 (1996) and Sasaki and Coy, 8 *Peptides* 119 (1987).

4. Rat Uterus functional assay

Trautshold, *Handbook of Expt. Pharmacol.* Vol 25, Springer Verlag pp 53–55 (1970) describes the Rat Uterus assay used to analyze the present compounds. The Trautshold method was used without changes to the parameters. U.S. Pat. No. 4,693,993, at Column 14, line 10 gives a general description of data analysis for this assay.

5. Guinea Pig Ileum functional assay

Trautshold, *Handbook of Expt. Pharmacol.* Vol 25, Springer Verlag pp 53–55 (1970) describes the Guinea Pig Ileum assay used to analyze the present compounds. The Trautshold method was used without changes to the parameters. U.S. Pat. No. 4,693,993, at Column 14, line 10 gives a general description of data analysis for this assay.

6. Data—the following data were obtained as indicated below:

| Compound | Uterus | Ileum |
|---|---|---|
| B10044 | I(8.1) | I(8.4) |
| B10056 | 9.5% | I(8.0) |
| B10058 | I(8.2) | I(7.9) |
| B10112 | 21% | I(7.6) |
| B10116 | I(8.2) | I(7.8) |
| B10118 | I(8.1) | I(8.3) |
| B10146 | Ag | I(5.9) |
| B10148 | I(7.2) | I(6.0) |
| B10150 | I(8.1) | I(7.9) |
| B10154 | I(8.2) | I(7.9) |
| B10156 | I(8.3) | I(7.9) |
| B10158 | I(8.5) | I(8.0) |
| B10164 | I(8.0) | I(7.2) |
| B10166 | I(8.1) | I(8.0) |
| B10168 | 4% | I(5.5) |
| B10172 | I(8.3) | I(7.3) |
| B10174 | I(8.1) | I(8.2) |
| B10178 | I(4.5) | I(6.4) |
| B10180 | I(8.2) | I(8.1) |
| B10186 | I(8.1) | I(7.4) |
| B10196 | I(7.9) | I(4.9) |
| B10204 | I(6.2) | I(7.9) |
| B10206 | I(8.9) | I(7.8) |
| B10208 | 14.0% | I(8.7) |
| B10210 | I(8.0) | I(7.8) |
| B10214 | I(8.2) | I(8.1) |
| B10216 | I(7.4) | I(6.8) |
| B10230 | I(5.8) | I(7.7) |
| B10232 | I(8.1) | I(7.7) |
| B10236 | I(7.7) | I(7.4) |

In this table, I=inhibitor, and numbers in parenthesis are $pA_2$. Agonist activity are given as percent BK activity. For example I(8.3) is an antagonist with a $pA_2$ of 8.3.

7. All of these compounds were effective bradykinin antagonists in the rat blood pressure model described by Roblero et al., 6 *Res. Comm. Chem. Pathol* 207 (1973.)

What is claimed is:

1. A compound of the formula:

$R_2$-$R_1$-A-B-C-D-E-F-G-H-I-J wherein:
$R_2$ is absent, or $GUN_2$; $R_1$ is absent, Lys, Aca or bApg; A is DArg, Lys or Arg; B is Arg; C is Pro or NMF; D is Hyp, Pro, Igl or DIgl; E is Gly; F is Igl, Thi, f5f or Cpg; G is Ser; H is Df5f, DIgl or DTic; I is Oic, Igl, Thi, NchG, f5f, Leu, Chg or Nc7G; and J is Arg, provided that, at least one of F, H or I must be f5f or Df5f.

2. A compound of claim 1, which is DArg-Arg-Pro-Hyp-Gly-Igl-Ser-Df5f-Oic-Arg.

3. A compound of claim 1, which is DArg-Arg-Pro-Hyp-Gly-Igl-Ser-Df5f-Igl-Arg.

4. A compound of claim 1, which is DArg-Arg-Pro-Hyp-Gly-Igl-Ser-Df5f-Thi-Arg.

5. A compound of claim 1, which is DArg-Arg-Pro-Hyp-Gly-Igl-Ser-Df5f-NchG-Arg.

6. A compound of claim 1, which is DArg-Arg-Pro-Pro-Gly-Thi-Ser-Df5f-Oic-Arg.

7. A compound of claim 2, wherein Formula I is Lys-DArg-Arg-Pro-Pro-Gly-Thi-Ser-Df5f-Oic-Arg and X is αDDD.

8. A compound of claim 1, which is Lys-Lys-Arg-Pro-Hyp-Gly-Igl-Ser-Df5f-Chg.

9. A compound of claim 1, which is Lys-Lys-Arg-Pro-Hyp-Gly-Igl-Ser-Df5f-Oic.

10. A compound of claim 1, which is DArg-Arg-NMF-Hyp-Gly-Igl-Ser-Df5f-Oic-Arg.

11. A compound of claim 1, which is Aca-DArg-Arg-Pro-Hyp-Gly-Igl-Ser-Df5f-Oic-Arg.

12. A compound of claim 1, which is Gun2-bApg-DArg-Arg-Pro-Hyp-Gly-Igl-Ser-Df5f-Oic-Arg.

13. A compound of claim 1, which is DArg-Arg-Pro-Hyp-Gly-f5f-Ser-DIgl-Oic-Arg.

14. A compound of claim 1, which is DArg-Arg-Pro-Hyp-Gly-Thi-Ser-Df5f-f5f-Arg.

15. A compound of claim 1, which is DArg-Arg-Pro-Hyp-Gly-Thi-Ser-DTic-f5f-Arg.

16. A compound of claim 1, which is DArg-Arg-Pro-Hyp-Gly-Thi-Ser-Df5f-Leu-Arg.

17. A compound of claim 1, which is DArg-Arg-Pro-Hyp-Gly-Igl-Ser-Df5f-Leu-Arg.

18. A compound of claim 1, which is DArg-Arg-Pro-Hyp-Gly-Igl-Ser-Digl-f5f-Arg.

19. A compound of claim 1, which is DArg-Arg-Pro-Hyp-Gly-Igl-Ser-Df5f-Chg-Arg.

20. A compound of claim 1, which is DArg-Arg-Pro-Hyp-Gly-Cpg-Ser-Df5f-Cpg-Arg.

21. A compound of claim 1, which is DArg-Arg-Pro-Hyp-Gly-Igl-Ser-Df5f-Cpg-Arg.

22. A compound of claim 1, which is DArg-Arg-Pro-Hyp-Gly-Thi-Ser-Df5f-Nc7G-Arg.

23. A compound of claim 1, which is DArg-Arg-Pro-Hyp-Gly-Igl-Ser-Df5f-Nc7G-Arg.

24. A compound of claim 1, which is DArg-Arg-Pro-Hyp-Gly-Thi-Ser-Df5f-NchG-Arg.

25. A compound of claim 1, which is DArg-Arg-Pro-Hyp-Gly-f5f-Ser-DIgl-Oic-Arg.

26. A compound of claim 1, which is DArg-Arg-Pro-Igl-Gly-Igl-Ser-Df5f-Oic-Arg.

27. A compound of claim 1, which is DArg-Arg-Pro-DIgl-Gly-Igl-Ser-Df5f-Oic-Arg.

28. A compound of claim 1, which is Arg-Arg-Pro-Hyp-Gly-Igl-Ser-Df5f-f5f-Arg.

29. A compound of claim 1, which is DArg-Arg-Pro-Hyp-Gly-Igl-Ser-Df5f-f5f-Arg.

30. A method to antagonize bradykinin receptors in a mammal in need of such antagonism, comprising administering a compound of claim 1.

31. A method to treat inflammation in a mammal in need of such treatment comprising administering a pharmaceutically-effective amount of a compound of claim 1.

* * * * *